(12) United States Patent
Cropper et al.

(10) Patent No.: US 8,197,404 B2
(45) Date of Patent: Jun. 12, 2012

(54) HANDOSCOPY INTERWOVEN LAYERED SEAL LAPAROSCOPIC DISK

(75) Inventors: Michael S. Cropper, Edgewood, KY (US); Paul T. Franer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 986 days.

(21) Appl. No.: 11/611,215

(22) Filed: Dec. 15, 2006

(65) Prior Publication Data

US 2008/0146882 A1    Jun. 19, 2008

(51) Int. Cl.
*A61B 1/32* (2006.01)
(52) U.S. Cl. ........................................................ 600/204
(58) Field of Classification Search ........... 600/201–246
See application file for complete search history.

(56) References Cited

U.S. PATENT DOCUMENTS

| | | |
|---|---|---|
| 563,645 A | 7/1896 | Bitting |
| 564,645 A | 7/1896 | Queen |
| 2,739,587 A | 3/1956 | Scholl |
| 3,111,943 A | 11/1963 | Orndorff |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 5,100,420 A | 3/1992 | Green et al. |
| 5,104,383 A | 4/1992 | Shichman |
| 5,171,249 A | 12/1992 | Stefanchik et al. |
| 5,197,955 A | 3/1993 | Stephens et al. |
| 5,292,330 A | 3/1994 | Shutt |
| 5,324,268 A | 6/1994 | Yoon |
| 5,337,754 A | 8/1994 | Heaven et al. |
| 5,366,478 A | 11/1994 | Brinkerhoff et al. |
| 5,385,552 A * | 1/1995 | Haber et al. ............. 604/167.03 |
| 5,437,683 A | 8/1995 | Neumann et al. |
| 5,460,170 A | 10/1995 | Hammerslag |
| 5,480,410 A | 1/1996 | Cuschieri et al. |
| 5,514,133 A | 5/1996 | Golub et al. |

(Continued)

FOREIGN PATENT DOCUMENTS

EP    0776180    6/1997

(Continued)

OTHER PUBLICATIONS

U.S. Appl. No. 11/538,325, filed Oct. 11, 2006, Lim et al.

(Continued)

*Primary Examiner* — Eduardo C Robert
*Assistant Examiner* — Steven Cotroneo
(74) *Attorney, Agent, or Firm* — Frost Brown Todd LLC

(57) ABSTRACT

A laparoscopic disk assembly, which includes an interwoven gasket seal, either flat or conical, comprised of four gasket sections, forms a seal without anything inserted or in the presence of a laparoscopic instrument or surgeon's hand, approximating an opening of a single through hole of a lip seal providing the same sealing as a lip seal. By breaking the seal through hole into multiple pieces, the direction and amount of strain applied to any section is less than the strain applied by the simple change in diameter. The layers form contact zones with the inserted probe or hand. The sum of the array of contact zones provides contact around the full diameter of the inserted tool or hand. Additionally, the hoop stress of the seal is reduced, thereby reducing the drag force on the instrument or the hand and wrist of the doctor.

10 Claims, 8 Drawing Sheets

U.S. PATENT DOCUMENTS

| | | | |
|---|---|---|---|
| 5,522,791 A | 6/1996 | Leyva | |
| 5,524,644 A | 6/1996 | Crook | |
| 5,526,536 A | 6/1996 | Cartmill | |
| 5,545,179 A | 8/1996 | Williamson, IV | |
| 5,640,977 A | 6/1997 | Leahy et al. | |
| 5,649,550 A | 7/1997 | Crook | |
| 5,653,705 A | 8/1997 | de la Torre et al. | |
| 5,653,717 A | 8/1997 | Ko et al. | |
| 5,672,168 A | 9/1997 | de la Torre et al. | |
| 5,741,298 A | 4/1998 | MacLeod | |
| 5,803,921 A | 9/1998 | Bonadio | |
| 5,810,721 A | 9/1998 | Mueller et al. | |
| 5,813,409 A | 9/1998 | Leahy et al. | |
| 5,817,062 A | 10/1998 | Flom et al. | |
| 5,853,395 A | 12/1998 | Crook et al. | |
| 5,899,208 A | 5/1999 | Bonadio | |
| 5,906,577 A | 5/1999 | Beane et al. | |
| 5,925,064 A | 7/1999 | Meyers et al. | |
| 5,947,922 A | 9/1999 | MacLeod | |
| 5,957,913 A | 9/1999 | de la Torre et al. | |
| 6,024,736 A | 2/2000 | de la Torre et al. | |
| 6,033,426 A | 3/2000 | Kaji | |
| 6,033,428 A | 3/2000 | Sardella | |
| 6,048,309 A | 4/2000 | Flom et al. | |
| 6,077,288 A | 6/2000 | Shimomura et al. | |
| 6,110,154 A | 8/2000 | Shimomura et al. | |
| 6,142,935 A | 11/2000 | Flom et al. | |
| 6,142,936 A | 11/2000 | Beane et al. | |
| 6,142,946 A | 11/2000 | Hwang et al. | |
| 6,149,642 A | 11/2000 | Gerhart et al. | |
| 6,159,200 A | 12/2000 | Verdura et al. | |
| 6,165,184 A | 12/2000 | Verdura et al. | |
| 6,228,022 B1 | 5/2001 | Friesem et al. | |
| 6,254,534 B1 | 7/2001 | Butler et al. | |
| 6,315,770 B1 | 11/2001 | de la Torre et al. | |
| 6,319,246 B1 | 11/2001 | de la Torre et al. | |
| 6,382,211 B1 | 5/2002 | Crook | |
| 6,440,063 B1 | 8/2002 | Beane et al. | |
| 6,450,983 B1 | 9/2002 | Rambo | |
| 6,485,467 B1 | 11/2002 | Crook et al. | |
| 6,536,277 B1 | 3/2003 | Chuang | |
| 6,540,983 B1 | 4/2003 | Adjei et al. | |
| 6,569,120 B1* | 5/2003 | Green et al. | 604/167.04 |
| 6,578,577 B2 | 6/2003 | Bonadio et al. | |
| 6,582,364 B2 | 6/2003 | Butler et al. | |
| 6,589,167 B1 | 7/2003 | Shimomura et al. | |
| 6,613,952 B2 | 9/2003 | Rambo | |
| 6,623,426 B2 | 9/2003 | Bonadio et al. | |
| 6,676,706 B1 | 1/2004 | Mears et al. | |
| 6,723,044 B2 | 4/2004 | Pulford et al. | |
| 6,808,520 B1 | 10/2004 | Fourkas et al. | |
| 6,814,078 B2 | 11/2004 | Crook | |
| 6,814,700 B1 | 11/2004 | Mueller et al. | |
| 6,846,287 B2 | 1/2005 | Bonadio et al. | |
| 2001/0037053 A1 | 11/2001 | Bonadio et al. | |
| 2001/0047188 A1 | 11/2001 | Bonadio et al. | |
| 2002/0002324 A1 | 1/2002 | McManus | |
| 2002/0010389 A1 | 1/2002 | Butler et al. | |
| 2002/0038077 A1 | 3/2002 | de la Torre et al. | |
| 2002/0068923 A1 | 6/2002 | Caldwell et al. | |
| 2002/0072762 A1 | 6/2002 | Bonadio et al. | |
| 2002/0152559 A1 | 10/2002 | Muirhead | |
| 2002/0183594 A1 | 12/2002 | Beane et al. | |
| 2003/0062051 A1 | 4/2003 | Rambo | |
| 2003/0078478 A1 | 4/2003 | Bonadio et al. | |
| 2003/0187376 A1 | 10/2003 | Rambo | |
| 2003/0192553 A1 | 10/2003 | Rambo | |
| 2004/0015185 A1 | 1/2004 | Ewers et al. | |
| 2004/0049099 A1 | 3/2004 | Ewers et al. | |
| 2004/0049100 A1 | 3/2004 | Butler et al. | |
| 2004/0064100 A1* | 4/2004 | Smith | 604/167.06 |
| 2004/0073090 A1 | 4/2004 | Butler et al. | |
| 2004/0092795 A1 | 5/2004 | Bonadio et al. | |
| 2004/0092796 A1 | 5/2004 | Butler et al. | |
| 2004/0093001 A1 | 5/2004 | Hamada | |
| 2004/0097793 A1 | 5/2004 | Butler et al. | |
| 2004/0127772 A1 | 7/2004 | Ewers et al. | |
| 2004/0154624 A1 | 8/2004 | Bonadio et al. | |
| 2004/0249248 A1 | 12/2004 | Bonadio et al. | |
| 2004/0254426 A1 | 12/2004 | Wenchell | |
| 2004/0260153 A1 | 12/2004 | Pulford et al. | |
| 2004/0267096 A1 | 12/2004 | Caldwell et al. | |
| 2005/0020884 A1* | 1/2005 | Hart et al. | 600/206 |
| 2005/0137460 A1 | 6/2005 | Bertolero et al. | |
| 2005/0148823 A1 | 7/2005 | Vaugh et al. | |
| 2005/0222582 A1* | 10/2005 | Wenchell | 606/108 |
| 2005/0241647 A1 | 11/2005 | Nguyen et al. | |
| 2005/0283050 A1* | 12/2005 | Gundlapalli et al. | 600/208 |
| 2006/0084842 A1* | 4/2006 | Hart et al. | 600/206 |
| 2006/0135977 A1* | 6/2006 | Thompson et al. | 606/185 |
| 2006/0247500 A1 | 11/2006 | Voegele et al. | |
| 2008/0009834 A1 | 1/2008 | Mialhe | |

FOREIGN PATENT DOCUMENTS

| | | |
|---|---|---|
| EP | 0845960 | 6/1998 |
| EP | 0887047 | 12/1998 |
| EP | 0887048 | 12/1998 |
| EP | 0888755 | 1/1999 |
| EP | 1000583 | 5/2000 |
| EP | 1135070 | 9/2001 |
| EP | 1312318 | 5/2003 |
| EP | 1415610 | 5/2004 |
| EP | 1442710 | 8/2004 |
| WO | WO 93/11811 | 6/1993 |
| WO | WO 95/22289 | 8/1995 |
| WO | WO 95/24864 | 9/1995 |
| WO | WO 95/27468 | 10/1995 |
| WO | WO 96/10963 | 4/1996 |
| WO | WO 97/07742 | 3/1997 |
| WO | WO 98/48724 | 11/1998 |
| WO | WO 99/03416 | 1/1999 |
| WO | WO 99/25268 | 5/1999 |
| WO | WO 00/24326 | 5/2000 |
| WO | WO 00/32116 | 6/2000 |
| WO | WO 00/32117 | 6/2000 |
| WO | WO 00/32120 | 6/2000 |
| WO | WO 00/54676 | 9/2000 |
| WO | WO 00/54677 | 9/2000 |
| WO | WO 01/08581 | 2/2001 |
| WO | WO 01/26558 | 4/2001 |
| WO | WO 01/45568 | 6/2001 |
| WO | WO 02/34108 | 5/2002 |
| WO | WO 03/028523 | 4/2003 |
| WO | WO 03/061480 | 7/2003 |
| WO | WO 03/077726 | 9/2003 |
| WO | WO 2004/026153 | 4/2004 |
| WO | WO 2004/030547 | 4/2004 |
| WO | WO 2004/054456 | 7/2004 |
| WO | WO 2004/075730 | 9/2004 |
| WO | WO 2004/075741 | 9/2004 |
| WO | WO 2004/096012 | 11/2004 |
| WO | WO 2004/103161 | 12/2004 |
| WO | WO 2005/009257 | 2/2005 |
| WO | WO 2006/061356 | 6/2006 |

OTHER PUBLICATIONS

Abstract for EP 0845960.

Abstract for EP 0776180.

Abstract for EP 1135070.

International Search Report dated May 28, 2008 for Application No. PCT/US2007/087372.

International Search Report dated May 29, 2008 for Application No. PCT/US2007/087385.

* cited by examiner

HANDOSCOPY INTERWOVEN LAYERED SEAL LAPAROSCOPIC DISK

CROSS REFERENCE TO RELATED APPLICATIONS

The present application is related to two commonly-owned U.S. patent applications filed on even date herewith, the disclosures of which are hereby incorporated by reference in their entirety: (1) Ser. No. 11/611,167, "Resiliently Supported Seal Cap for Hand Assisted Laparoscopic Surgical Procedures" to Kistler et al.; and (2) Ser. No. 11/611,193, "Fully Automated Iris Seal for Hand Assisted Laparoscopic Surgical Procedures" to Beckman et al.

FIELD OF THE INVENTION

The invention generally relates to surgical access systems that facilitate sealed access across a body wall and into a body cavity during a laparoscopic surgical procedure.

BACKGROUND OF THE INVENTION

In the practice of abdominal surgery, which requires the examination and manipulation of intraperitoneal and extraperitoneal organs and tissues, surgeons most often employ a long established technique of opening the abdominal wall with an incision large enough to accommodate instruments required, as well as the surgeon's hands, and to allow procedures such as anastomosis or removal of diseased organs or portions thereof. The advantages of this technique include a large degree of freedom of motion for successfully completing the procedure, sufficient space for mechanical leverage which may be necessary, and above all, tactile feedback response to the surgeon when using his hands to feel the texture, temperature, and physical response of the tissues. The disadvantages of this traditional technique, however, include long healing and recuperative time with considerable post-operative pain, and adhesion formation which can cause pain and bowel obstruction. Additionally, the traditional technique may increase the complexity of later surgery, as well as increase the possibility of post-operative morbidity and unsightly scars remaining after the procedure is completed.

In order to overcome the disadvantages of the traditional abdominal surgery method using a large incision, laparoscopic techniques have been developed which use several smaller puncture openings in the abdominal wall. These openings are used to inflate the abdominal cavity with a gas to elevate the abdominal wall away from the organs, and to allow room for the manipulation of the organs. The openings also provide means to introduce light generating and optical viewing instruments to observe the abdominal cavity, and to manipulate the organs in order to accomplish the desired results. This laparoscopic technique is becoming widely accepted because of its many advantages. These advantages include reduced adhesions, shorter recovery time, and less post-operative pain. There are also some disadvantages. For example, there are limitations on freedom to manipulate organs, and on the surgeon's viewing ability which, although magnified with the aid of a laparoscope, lacks depth perception. Most importantly, there is a lack of tactile feedback of the tissue through the surgeon's hands. Also, when a tissue specimen must be removed, a larger opening must be made in the abdominal wall near the end of the procedure, causing loss of gas pressure, collapse of the abdominal wall, and loss of interior working and viewing space.

The laparoscopic technique uses smaller puncture openings in the abdominal wall as described. These openings are usually made with a puncture device called a trocar. The trocar point and attached shaft are usually contained in a hollow circular tube which remains in the abdominal wall after puncture and through which other instrument shafts are passed to be used in the operating procedure. A sealing feature must be included in the trocar cannula body in order to maintain the gas pressure as described above. Various sizes and shapes of instruments are used in these procedures and sealing between the instruments and the trocar body must be achieved. Also, internal sealing is required within the instrument body passing through the cannula to avoid gas leakage. The importance of these sealing requirements is indicated by their inclusion in endoscopic instrument patents. For example, U.S. Pat. Nos. 5,104,383 and 5,197,955, describe sealing mechanisms between trocars and instruments passed through them. Also, the endoscopic instruments themselves contain internal sealing means to reduce the loss of gas pressure in the abdominal cavity. U.S. Pat. Nos. 5,100,420 and 5,171,249, describe internal sealing means in endoscopic instruments.

The laparoscopic assisted procedure combines the advantages of the traditional and the laparoscopic techniques for abdominal surgery. In this procedure, the normal laparoscopic small puncture openings are made with the exception that one opening is made large enough to allow a surgeon's hand to pass through the abdominal wall in order to remove tissue or deliver a mobile organ for transplant surgery. This procedure is now called handoscopy.

When this larger opening is made, a sealing device designed and sized to both fit within the incision and allows a surgeon to pass through his hand into the abdominal space with minimal loss of gas pressure.

Several surgical devices are described in patents such as Brinkerhoff—U.S. Pat. No. 5,366,478, Shimomura—U.S. Pat. No. 6,077,288, and MacLeod—U.S. Pat. No. 5,741,298. With all of these devises, the surgeon must use two hands to insert his one hand into the patient while at the same time potentially losing all of the insufflation gas from within the abdomen.

Accordingly, one object of the present invention is to allow the advantages of the laparoscopic method of maintaining gas pressure in the abdominal cavity, and of requiring relatively small incisions for quicker recovery than the traditional method, yet it allows the surgeon the important feature of tactile feedback to determine directly the information needed to successfully conclude the procedure as well as allow removal of the specimen.

In U.S. Pat. Appln. Publ. No. 2005/0020884, versions of transverse, overlapping partial seals are disclosed that address the need to a degree for a seal accessible with one hand without significant loss of insufflation pressure, but additional improvements are desirable.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

procedure by the insertion of a laparoscopic disk incorporating an interwoven gasket seal consistent with aspects of the invention.

Figure 1:
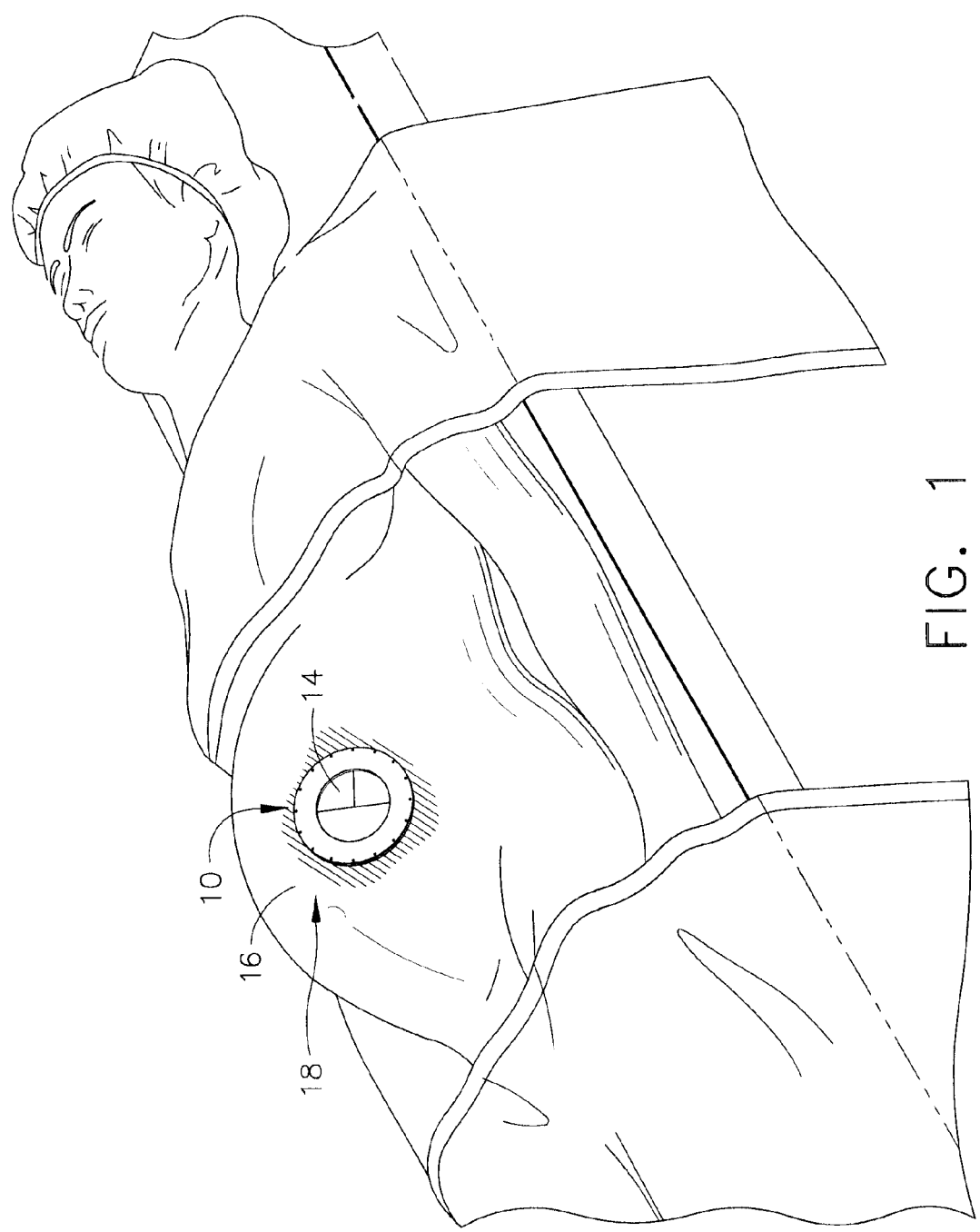
FIG. 1 is an environmental perspective view of a patient prepared for a Hand Assisted Laparoscopic Surgery (HALS)
Figure 2:
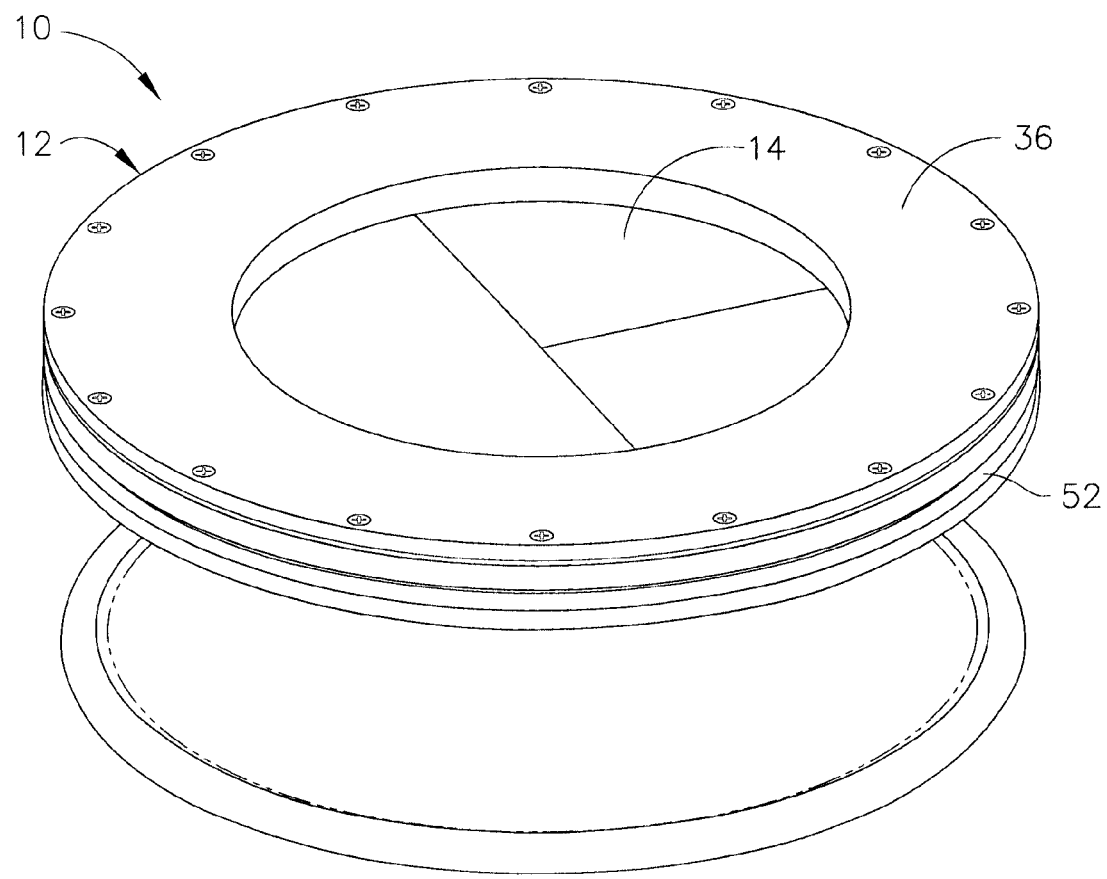

FIG. 2 is a perspective view of a HALS laparoscopic disk assembly that includes the laparoscopic disk of FIG. 1 attached to a retraction skirt.

Figure 3:
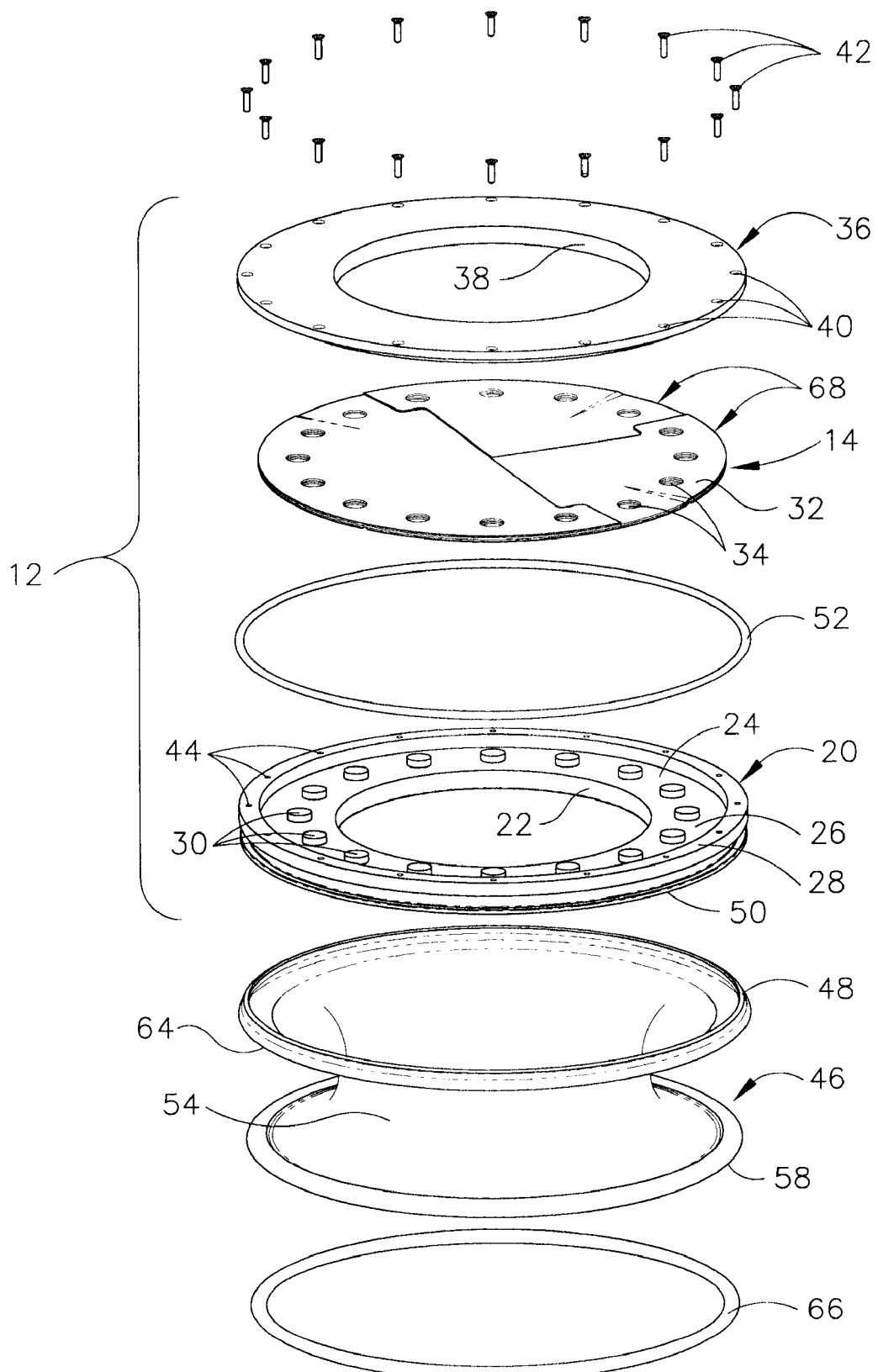

FIG. 3 is an exploded perspective view of the HALS laparoscopic disk assembly of FIG. 2.

Figure 4:
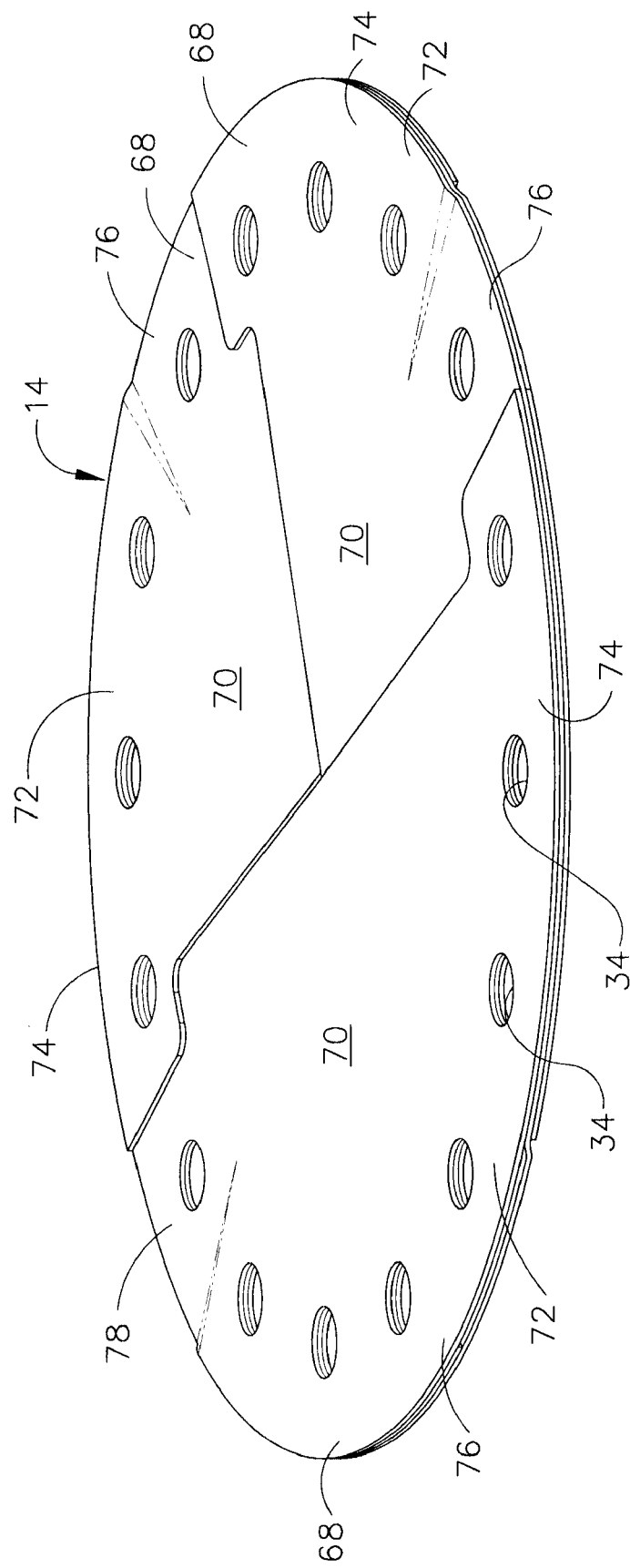

FIG. 4 is a perspective view of the interwoven gasket seal of the laparoscopic disk of FIG. 1.

Figure 5:
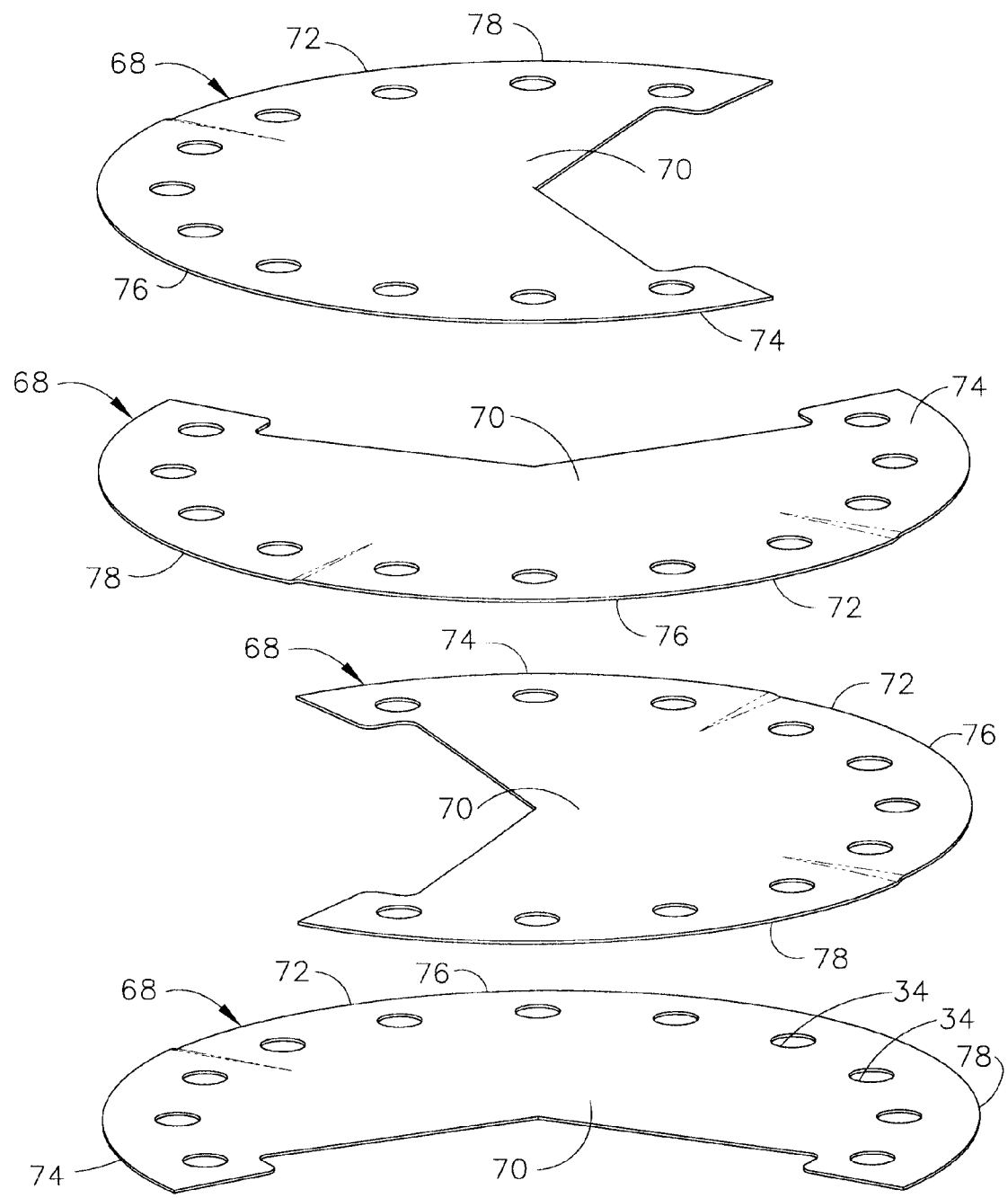

FIG. 5 is a perspective, exploded view of the interwoven gasket seal of the laparoscopic disk of FIG. 1.

Figure 6:
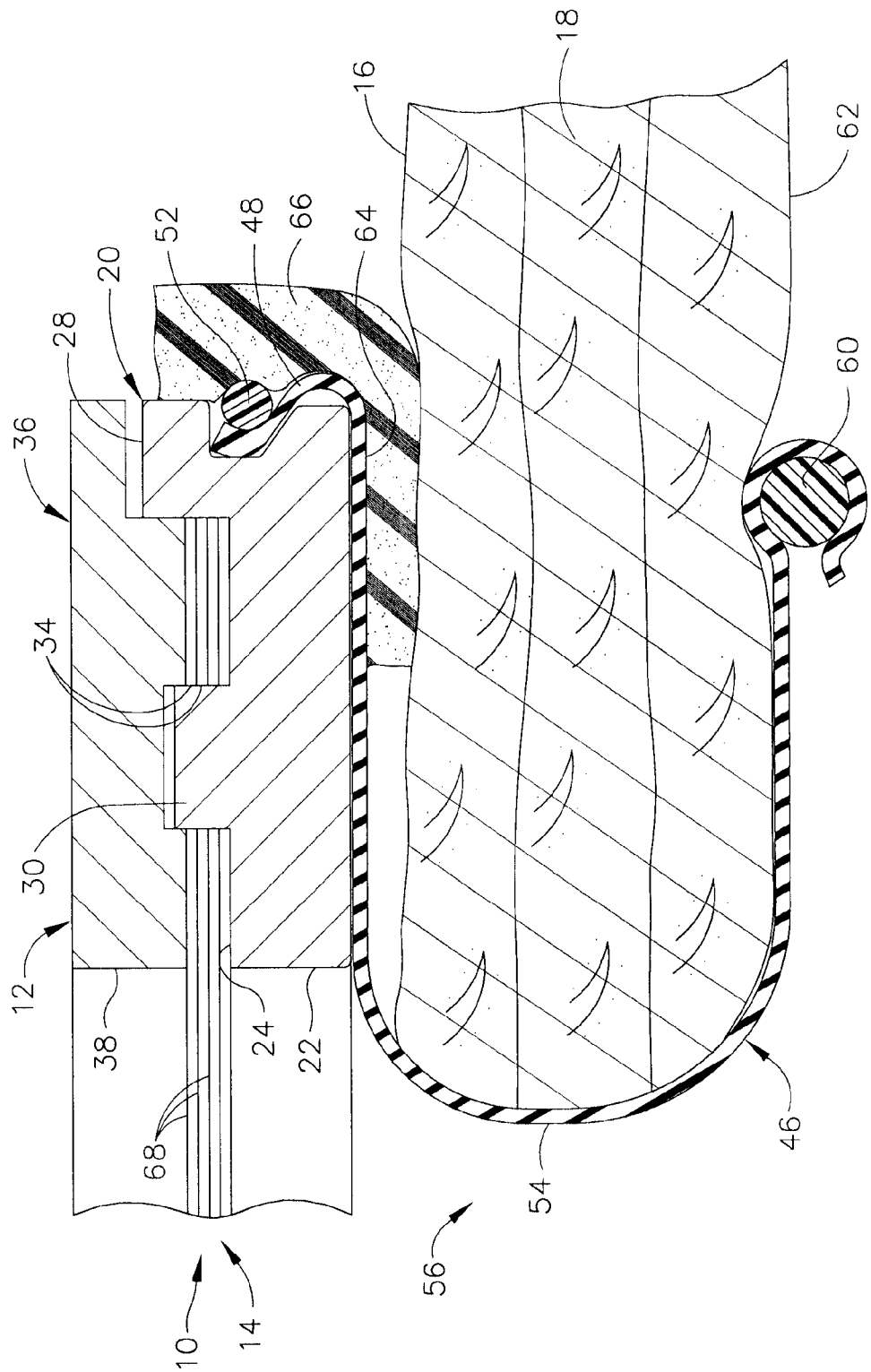

FIG. 6 is a right side view in cross section of a left side of the laparoscopic disk assembly of FIG. 1 inserted into an incision through an abdominal wall of the patient.

Figure 7:
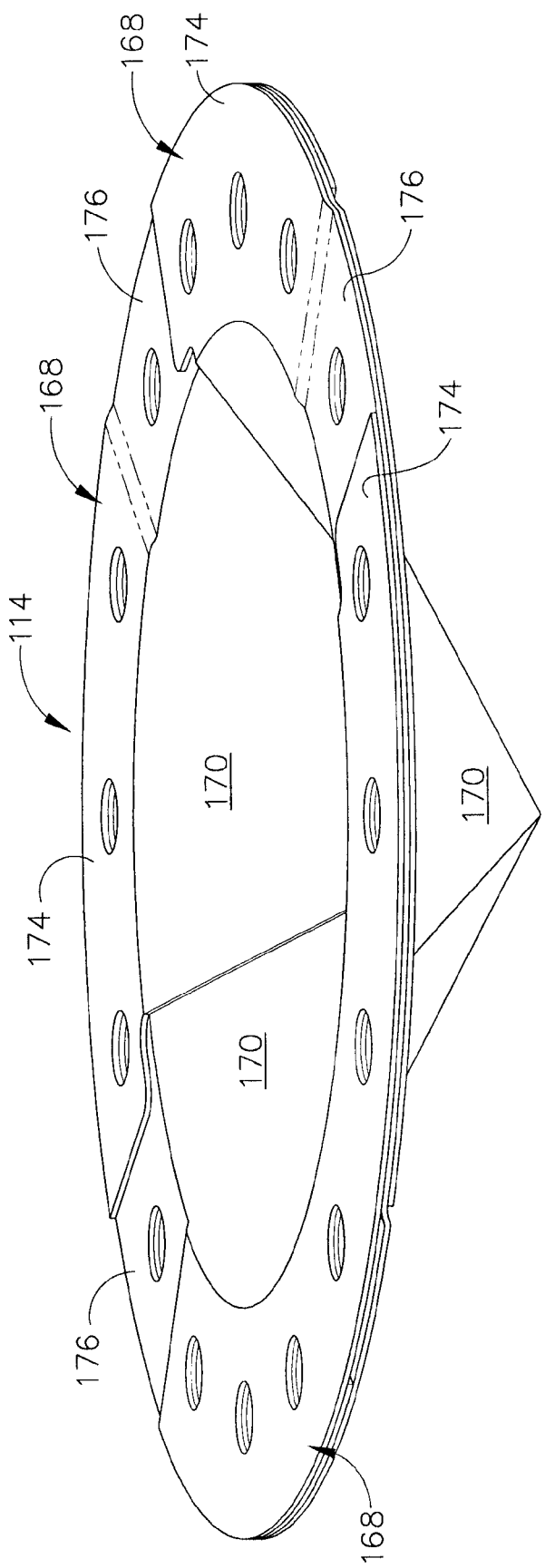

FIG. 7 is a perspective view of an alternative conical, interwoven gasket seal for the laparoscopic disk of FIG. 1.

Figure 8:
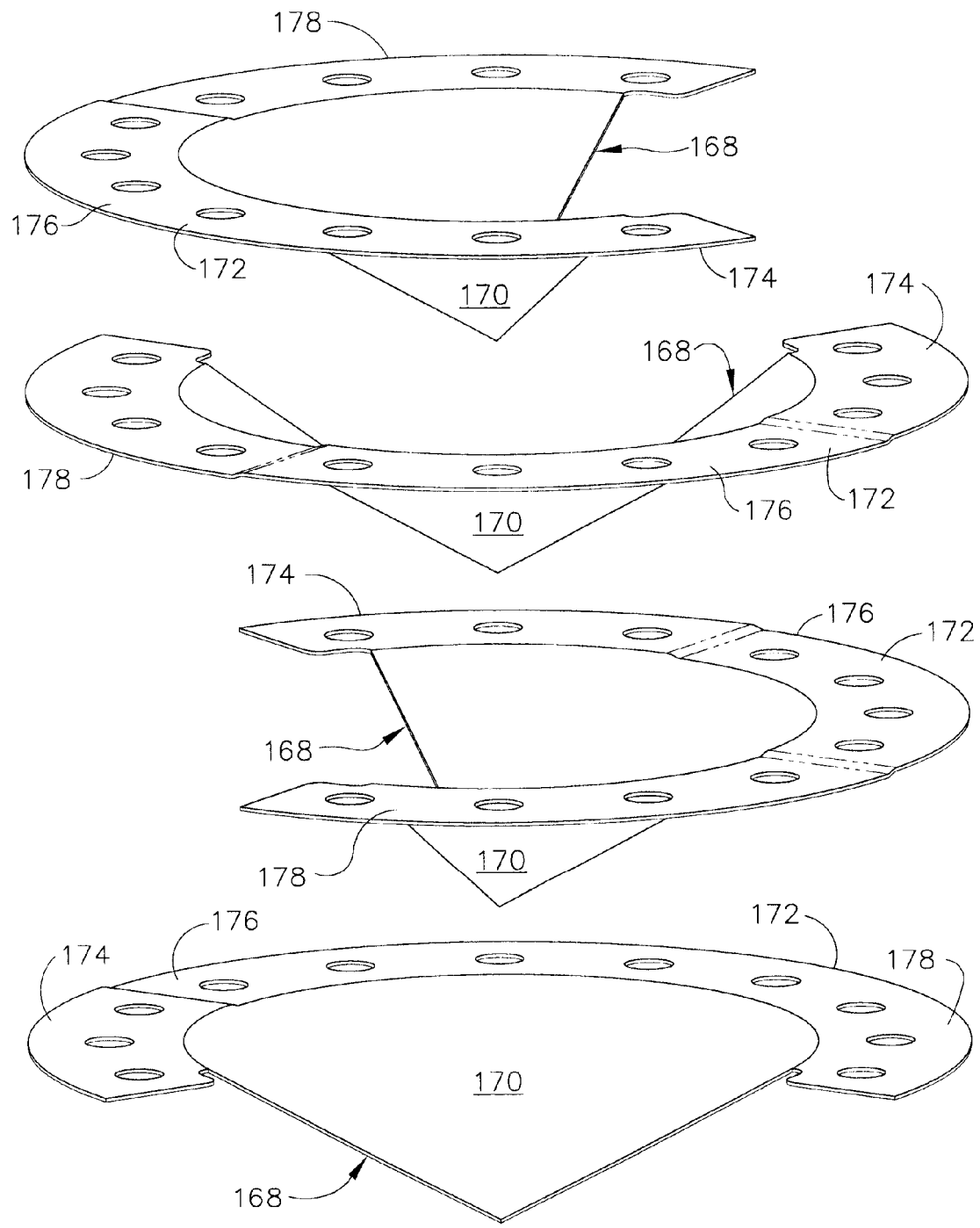

FIG. 8 is a perspective, exploded view of the alternative conical, interwoven gasket seal of FIG. 7.

DETAILED DESCRIPTION OF THE INVENTION

Referring now to FIG. 1, the environment for performing an endoscopic surgical procedure within an abdomen is illustrated, herein referred to as Hand Assisted Laparoscopic Surgery (HALS). A surgeon places a hand through a surgical access device depicted as a HALS laparoscopic disk assembly 10 that includes an exteriorly visible laparoscopic disk (seal cap) 12 that retains a flat interwoven gasket seal 14 that forms a valve defining an access channel expansive enough to admit a surgeon's hand without having to use the other hand to effect opening or closing and thereby, maintaining gas pressure during any laparoscopic, and more particularly, laparoscopic assisted procedure. The laparoscopic disk is positioned upon an exterior surface 16 of patient's abdominal wall 18.

The flat interwoven gasket seal 14 forms a seal without anything inserted or in the presence of a laparoscopic instrument or surgeon's hand, approximating an opening of a single through hole of a lip seal and provide the same sealing as a lip seal. By breaking the seal through hole into multiple pieces, the direction and amount of strain applied to any section is less than the strain applied by the simple change in diameter. The layers form contact zones with the inserted probe or hand. The sum of the array of contact zones provides contact around the full diameter of the inserted tool or hand. Additionally, the hoop stress of the seal is reduced, thereby reducing the drag force on the instrument. It is the reduction of the hoop stress that will facilitate the insertion of a hand and wrist into the patient.

In FIGS. 2-3, the laparoscopic disk assembly 10 includes a base ring 20 having an aperture 22 centered within an inner annular gasket recess 24 defined upon a top surface 26 within a raised outer annular mounting surface 28. Radially spaced, squat cylindrical posts 30 are formed within the inner annular gasket recess 24 to approximate the height of the surrounding outer annular mounting surface 28. The flat interwoven gasket seal 14 includes an outer annular mounting flange 32 having a composite thickness and radial annular width approximately equal to the depth and radial width respectively of the inner annular gasket recess 24. The outer annular mounting flange 32 has mounting holes 34 sized and registered to receive a respective squat cylindrical post 30. A top ring 36 has an aperture 38 and a radial annular width that corresponds to the base ring 20. A plurality of radially spaced through holes 40 about a periphery of the top ring 36 each receive a fastener (e.g., bolt) 42 that pass on through to be engaged within a respective one of a plurality of radially spaced bolt holes 44 formed in the outer annular mounting surface 28.

In FIGS. 3 and 6, the laparoscopic disk assembly 10 further includes a retractor skirt 46 which has an upward lip 48 sized to slip over and to enter an outer ring groove 50 formed into the base ring 20, held therein by an O-ring 52. A narrowed waist portion 54 of the retractor skirt 46 comprises a venturi-shaped tube formed of resilient material that retracts a wound or incision 56 through the abdominal wall 18. A lower opening 58 of the retractor skirt 46 is defined by a flexible ring 60 (FIG. 6) that forms a lip of the retractor skirt 46 and is wider than the resilient waist portion 54 thereof to contact an inner surface 62 of the abdominal wall 18 around the incision 56. The flexible ring 60 allows insertion in a deformed state through the incision 56 with subsequent rebounding to the depicted relaxed, circular shape.

A downward annular surface 64 of the laparoscopic disk 12 is supported by an attached flexible or resilient ("soft") support member 66 that forms an annular sealing contact upon the exterior surface 16 of the patient's abdominal wall 18 surrounding the incision 56. Versions of the soft support member 66 are described in greater detail in the cross referenced U.S. patent application Ser. No. 11/611,167.

In FIGS. 4-5, the flat interwoven gasket seal 14 consists of four identical multiple, interwoven gasket sections 68, each having an inwardly projecting partial barrier portion 70 from a partial mounting flange 72. It should be appreciated that applications consistent with aspects of the invention may incorporate less than or more than four gasket sections 68 with appropriate angular portions provided by each gasket section 68 for a suitable overlap. In the illustrative version, each gasket section 68 has the partial mounting flange 72 and partial barrier portion 68 of slightly more than 270° resembling a circle with a pie-shaped portion removed. The partial mounting portion 72 has three stepped portions 74, 76, 78 with the highest stepped portion 74 being counterclockwise when viewed from above and the lowest stepped portion 78 being clockwise. Thus, each gasket section 68 is stacked with a quarter turn clockwise relative to the gasket section 68 immediately below. This interwoven configuration enables a spiraling dilation to be formed as an instrument or a hand is inserted through the flat interwoven gasket seal 14.

The four gasket sections 68 overlap such that there is almost no hole in the center allowing for minimal leakage of $CO_2$ from the abdomen and form a complete seal. Thereby, the multi-piece gasket seal 14 enables easy insertion of the surgeons' hand into the patient during the procedure, yet seals around the wrist and maintain the abdominal insufflation. Upon withdrawal of the hand, the laparoscopic disk assembly 10 closes off and reduces the leak rate to a manageable value of approximately 1000 cc/min. The gasket sections 68 may be radially stretched during assembly ("pre-stretching") to promote sealing between adjacent seal sections 68 by urging the sections 68 to contact one another without the presence of an arm.

In FIGS. 7-8, an alternative conical, interwoven gasket seal 114 consists of four identical multiple, interwoven gasket sections 168, each projecting downwardly a partial conical portion 170 from a partial mounting flange 172. It should be appreciated that applications consistent with aspects of the invention may incorporate less than or more than four gasket sections 168 with appropriate angular portions provided by each gasket section 168 for a suitable overlap. In the illustrative version, each gasket section 168 has the partial mounting flange 172 and partial conical portion 168 of slightly more than 270°, the latter resembling a circle with a pie-shaped portion removed. The partial mounting portion 172 has three stepped portions 174, 176, 178 with the highest stepped portion 174 being counterclockwise when viewed from above and the lowest stepped portion 178 being clockwise. Thus, each gasket section 168 is stacked with a quarter turn clockwise relative to the gasket section 168 immediately below. This interwoven configuration enables a spiraling dilation to be formed as an instrument or a hand is inserted through the conical, interwoven gasket seal 114.

For clarity, the laparoscopic disks 12, 116 depicted above omit a seal protector that prevents a sharp tipped instrument that strikes off center from cupping and piercing resilient material of the gasket sections 68, 168. To avoid seal degradation, an outer seal protector may be positioned outward from the gasket sections 68, 168 and shaped to guide an inserted instrument toward the center ("septum") of the gasket sections 68, 168. Alternatively the seal protector may be formed of a material that prevents penetration of the outer portions of the gasket sections 68, 168 but does not serve to guide the instrument to the center of the gasket sections 68, 168, relying upon the surgeon to visually reposition the instrument.

The protectors that are proximal to the seal components also transfer a distributed force to the seal sections. An inserted instrument applies force to the protectors through contact and the protectors then apply a distributed normal force to much of the opposing seal surfaces that are contacted by the protectors. Since the seal gasket sections apply a resistive force to this movement due to stretching of an elastomeric material, the seal layers are compressed against one another promoting sealing by reducing or eliminating any gaps that might exist between adjacent seal layers, attaining a good seal. Without such protectors, the only contact force with the seal sections is at the region of instrument contact with the seal sections. A large portion of the seal surface area thus are not forced together, which may serve as a leak path during instrument extraction where the seal layers tend to separate. With the protectors in place, the seal layers are held together even during instrument extraction.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, while a circular disk is depicted in the illustrative version, applications consistent with the present invention may comprise other geometric shapes (e.g., octagonal, square).

What is claimed is:

1. A surgical access device adapted for disposition relative to an incision in a patient, the surgical access device comprising:
a valve including a plurality of interwoven, overlapping sheets defining an access channel, wherein each of the sheets has a respective mounting flange, wherein each of the sheets further comprises an elastic barrier portion extending from the respective mounting flange, wherein the mounting flange of each sheet comprises at least two mounting flange portions separated by a step having a height at an outermost radial position, wherein the height of the step tapers as the radial distance from a center of the valve decreases, wherein the elastic barrier portions of the plurality of interwoven, overlapping sheets together define a conical shape;
an upper ring; and
a base ring having an inner diameter for holding the valve by fixing each of the overlapping sheets along a portion of the perimeter, wherein the base ring has a first upper surface and a second upper surface, wherein the second upper surface is lower than the first upper surface such that the second upper surface defines an annular recess, wherein the mounting flanges are stacked in the annular recess, wherein the upper ring is coupled to the first upper surface of the base ring to secure the stacked mounting flanges in the annular recess,
wherein the access channel is configured to provide access through the incision in the patient.

2. The surgical access device of claim 1, wherein the plurality of interwoven, overlapping sheets comprises at least three sheets, wherein the mounting flange of each sheet comprises an arcuate portion sized for engagement to at least two thirds of a circumference of the inner diameter of the ring, each elastic barrier portion defining an acute angle.

3. The surgical access device of claim 1, wherein each sheet comprises a radially stretched member during assembly.

4. The surgical access device of claim 1, wherein the at least two mounting flange portions separated by a step are configured for maintaining a uniform stacked thickness with overlapping adjacent sheets.

5. The surgical access device of claim 1, wherein the plurality of interwoven, overlapping sheets comprises four identical sheets, each sheet rotated ninety degrees in a selected direction with any immediately underlying sheet.

6. A surgical access device adapted for disposition relative to an incision in a patient, the surgical access device comprising:
an outer frame, wherein the outer frame comprises:
an upper ring, and
a base ring, wherein the base ring has a first upper surface and a second upper surface, wherein the second upper surface is lower than the first upper surface such that the second upper surface defines an annular recess; and
a valve including a plurality of interwoven, overlapping sheets defining an access channel that is configured to provide access through the incision in the patient, each of the plurality of sheets being rotated relative to any overlying sheet and to any underlying sheet, wherein each of the sheets has a respective mounting flange having at least two mounting flange portions, wherein each mounting flange has a first mounting flange portion is positioned within a first horizontal plane, wherein each mounting flange has the second mounting flange portion is positioned in a second horizontal plane, wherein the first mounting flange portion and the second mounting flange portion are joined by a step, wherein the step tapers such that the first mounting flange and the second mounting flange are coplanar at a point radially inset from an exterior edge of the respective sheet, wherein each of the sheets further comprises an elastic barrier portion extending from the respective mounting flange, wherein the elastic barrier portions of the plurality of interwoven, overlapping sheets together define a downwardly extending conical shape, wherein the mounting flanges are stacked in the annular recess, wherein the upper ring is coupled to the first upper surface of the base ring to secure the stacked mounting flanges in the annular recess.

7. The surgical access device of claim 6, wherein the plurality of interwoven, overlapping sheets comprises at least three sheets.

8. The surgical access device of claim 6, wherein each sheet comprises a radially stretched member during assembly.

9. The surgical access device of claim 6, wherein the at least two mounting flange portions are configured for maintaining a uniform stacked thickness with overlapping adjacent sheets.

10. The surgical access device of claim 6, wherein the plurality of interwoven, overlapping sheets comprises four identical sheets, each sheet rotated ninety degrees in a selected direction with any immediately underlying sheet.

* * * * *